(12) United States Patent
Gross et al.

(10) Patent No.: US 8,796,228 B2
(45) Date of Patent: Aug. 5, 2014

(54) METHOD FOR NEUTRALIZING FUNGI USING SOPHOROLIPIDS AND ANTIFUNGAL SOPHOROLIPIDS FOR USE THEREIN

(75) Inventors: Richard A. Gross, New York, NY (US); Vishal Shah, Oakdale, NY (US)

(73) Assignee: Synthezyme, LLC, Troy, NY (US)

( * ) Notice: Subject to any disclaimer, the term of this patent is extended or adjusted under 35 U.S.C. 154(b) by 0 days.

(21) Appl. No.: 12/360,486

(22) Filed: Jan. 27, 2009

(65) Prior Publication Data
US 2009/0186836 A1 Jul. 23, 2009

Related U.S. Application Data

(63) Continuation of application No. 11/020,683, filed on Dec. 22, 2004, now abandoned.

(51) Int. Cl.
*A61K 31/70* (2006.01)

(52) U.S. Cl.
USPC .......................................................... 514/25

(58) Field of Classification Search
None
See application file for complete search history.

(56) References Cited

U.S. PATENT DOCUMENTS

| | | | |
|---|---|---|---|
| 4,297,340 A * | 10/1981 | Abe et al. ...................... | 424/70.1 |
| 5,514,661 A | 5/1996 | Piljac et al. | |
| 5,597,573 A | 1/1997 | Kamireddy et al. | |
| 5,648,343 A | 7/1997 | Carlson | |

OTHER PUBLICATIONS

Bisht et al (J Org Chem 64:780-789, 1999).*
www.emedicinehealth.com (available online, accessed Jan. 12, 2011).*
Kim et al. "Characteristics of Sophorolipids as an antimicrobial agent" J. Microgiol, Biotechnol (Apr. 2002) 12(2): 235-241.
Bisht et al. "Enzyme-mediated regioselective acylations of sophorolipids" J. Org. Chem. (1999) 64: 780-789.
Gorin, P.A., et al., Can. J. Chem., vol. 39, p. 846 (1961).
Davila, A.M. et al., J. Chromatogr., vol. 648, p. 139 (1993).
Tulloch, A.P. et al., Can. J. Chem., vol. 40, p. 1326 (1962).
Tulloch, A.P. et al., Can. J. Chem., vol. 46, p. 3337 (1968).
Zhou, Q.-H. et al, J. Am. Oil Chem. Soc., vol. 72, p. 67 (1995).
Rau, U. et al., Biotechnol. Lett., vol. 18, p. 149 (1996).

* cited by examiner

*Primary Examiner* — Craig Ricci
(74) *Attorney, Agent, or Firm* — Laurence P. Colton; Smith Risley Tempel Santos LLC

(57) ABSTRACT

17-L-[(2'-O-β-D-glucopyranosyl-β-D-glucopyranosyl)-oxy]-cis-9-octa-decenoate, lactonic and open ring 17-L-[(2'-O-β-D-glucopyranosyl-β-D-glucopyranosyl)-oxy]-cis-9-octadecenoate, methyl 17-L-[(2'-O-β-D-glucopyranosyl-β-D-glucopyranosyl)-oxy]-cis-9-octadecenoate, ethyl 17-L-[(2'-O-β-D-glucopyranosyl-β-D-glucopyranosyl)-oxy]-cis-9-octadecenoate, hexyl 17-L-[(2'-O-β-D-glucopyranosyl-β-D-glucopyranosyl)-oxy]-cis-9-octadecenoate, ethyl 17-L-[(2'-O-β-D-glucopyranosyl-β-D-glucopyranosyl)-oxy]-cis-9-octadecenoate-6"-acetate and ethyl 17-L-[(2'-O-β-D-glucopyranosyl-β-D-glucopyranosyl)-oxy]-cis-9-octadecenoate-6',6"-diacetate sophorolipids and uses thereof as antifungal agents.

3 Claims, 1 Drawing Sheet

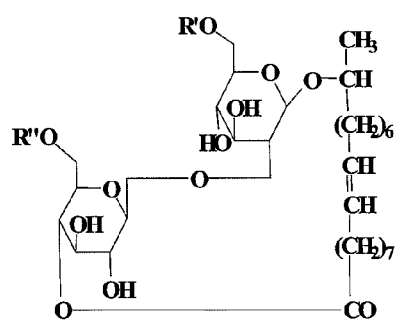
1. R' = R'' = Ac or H
2. R' = Ac; R'' = H
3. R' = H; R'' = Ac
4. R' = R'' = H
1A. Lactonic sophorolipid
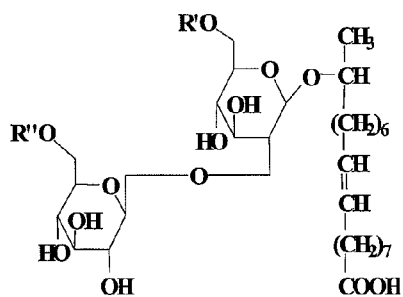
5. R' = R'' = Ac or H
6. R' = Ac; R'' = H
7. R' = H; R'' = Ac
8. R' = R'' = H
1B. Open ring sophorolipid
**Structures of sophorolipids produced by *Candida bombicola*.**

METHOD FOR NEUTRALIZING FUNGI USING SOPHOROLIPIDS AND ANTIFUNGAL SOPHOROLIPIDS FOR USE THEREIN

STATEMENT OF RELATED APPLICATIONS

This patent application is a continuation of U.S. patent application Ser. No. 11/020,683, filed on 22 Dec. 2004, abandoned, which is the National Stage of International Application No. PCT/US2003/035871, filed on 6 Nov. 2003.

BACKGROUND OF THE INVENTION

1. Technical Field

The present invention generally relates to the field of sophorolipids having anti-fungal properties and more specifically relates to methods for using such sophorolipids as anti-fungal agents. The invention also relates to 17-L-[(2'-O-β-D-glucopyranosyl-β-D-glucopyranosyl)-oxy]-cis-9-octadecenoate based sophorolipids and their uses as anti-fungal agents.

2. Prior Art

First described in 1961, sophorolipids occurs as a mixture of macrolactone and free acid structures that are acetylated to various extents at the primary hydroxyl position of the sophorose ring. Gorin, P. A. et al., Can. J. Chem., vol. 39, p. 846 (1961). Careful examinations have revealed that at least eight structurally different sophorolipids are produced. Davila, A. M. et al., J. Chromatogr., vol. 648, p. 139 (1993). The main component of sophorolipids is 17-hydroxyoctadecanoic acid and its corresponding lactone. Tulloch, A. P. et al., Can. J. Chem., vol. 40, p. 1326 (1962) and Tulloch, A. P. et al., Can J. Chem., vol. 46, p. 3337 (1968).

Work has been carried out to tailor sophorolipid structure during in vivo formation, mainly by the selective feeding of different lipophilic substrates. Zhou, Q.-H., et al., J. Am. Oil Chem. Soc., vol. 72, p. 67 (1995). Also unsaturated C-18 fatty acids of oleic acid may be transferred unchanged into sophorolipids. Rau, U. et al., Biotechnol. Lett., vol. 18, p. 149 (1996). However, while physiological variables during fermentation have provided routes to the variation of sophorolipid composition, this has not led to well-defined pure compounds.

Existing data suggests that glycolipids may be useful in treating very severe immune disorders. For example, glycolipids have been reported to be of interest for in vivo cancer treatment/antitumor cell activity, treatment of autoimmune disorders, in vivo and in vitro anti-endotoxic (septic) shock activity, regulation of angiogenesis, and apoptosis induction, all by cytokine activity. See, e.g., U.S. Pat. No. 5,597,573 to Massey, U.S. Pat. No. 5,514,661 to Piljac, U.S. Pat. No. 5,648,343 to Carlson, and the references cited in notes 9-13 of Bisht, K. S. et al., J. Org. Chem., vol. 64, pp. 780-789 (1999).

Thus, there exists a need to develop new and improved treatments for various human disorders using glycolipids. It is to the development of sophorolipids for these treatments, for other pharmaceutical and industrial purposes, and for other purposes, that the present invention is directed.

BRIEF SUMMARY OF THE INVENTION

Sophorolipids are microbial extracellular glycolipids produced by resting cells of *Candida bombicola*. The chemical composition of sophorolipid is constituted by a disaccharide sugar viz. sophorose and a fatty acid or an ester group. *Candida bombicola* produces the sophorolipids as a mixture of macroloctones and free acid structures that are acetylated to various extents at the primary hydroxyl sophorose ring positions (FIG. 1). Bisht, K. S. et al., J. Org. Chem., vol. 64, pp. 780-789 (1999).

In the present invention, a natural mixture of sophorolipids is synthesized by fermentation of *Candida bombicola*. Lactonic sophorolipid was separated from the natural mixture. Also, the natural mixture was treated to obtain open ring sophorolipid. Ethyl 17-L-[(2'-O-β-D-glucopyranosyl-β-D-glucopyranosyl)-oxy]-cis-9-octadecenoate then was synthesized and then further treated to obtain Ethyl 17-L[(2'-O-β-D-glucopyranosyl-β-D-glucopyranosyl)-oxy]-cis-9-octadecenoate 6',6"-diacetate. Ethyl 17-L-[(2'-O-β-D-glucopyranosyl-β-D-glucopyranosyl)-oxy]-cis-9-octadecenoate-6"-acetate also was synthesized by adding lipase to a solution of ethyl ester, (325.4 mg) and vinyl acetate (230.9 μl) in dry THF (5 ml), and further treatment. Hexyl 17-L-[(2'-O-β-D-glucopyranosyl-β-D-glucopyranosyl)-oxy]-cis-9-octadecenoate and methyl 17-L-[(2'-O-β-D-glucopyranosyl-β-D-glucopyranosyl)-oxy]-cis-9-octadecenoate also were synthesized.

Various organisms were treated with the sophorolipids and the ability of the sophorolipids to inhibit growth of the organisms was measured. The ability of various forms of sophorolipids to inhibit the growth of organisms varies depending on the type of organism under test. As all sophorolipids have been found to be selectively active against certain forms of organisms, the applications of sophorolipids in field of medicine would be tremendous to treat various infections, apart from other applications. Further, while sophorolipids can find applications in diverse fields, the present invention indicates that sophorolipids can be used as anti-fungal agents.

These features, and other features and advantages of the present invention, will become more apparent to those of ordinary skill in the relevant art when the following detailed description of the preferred embodiments is read in conjunction with the appended drawing.

BRIEF DESCRIPTION OF THE FIGURE

FIG. 1 are representative structures of sophorolipids produced by *Candida bombicola*, with FIG. 1A showing lactonic sophorolipid and FIG. 1B showing open ring sophorolipid.

DETAILED DESCRIPTION OF THE PREFERRED EMBODIMENTS

1. Sophorolipid Fermentation

Sophorolipids were synthesized by fermentation of *Candida bombicola*. The fermentation media was composed of 100 g glucose, 10 g yeast extract, 1 g urea and 40 g oleic acid in 1000 ml of water. After 7 days of fermentation, sophorolipid was extracted thrice using ethyl acetate. The extracts were pooled and the solvent then was removed. The obtained product then was washed with hexane to remove the residual fatty acids. This was "natural" sophorolipid. The sophorolipid was dried in a vacuum desiccator.

2. Preparation of Lactonic Sophorolipid

Column chromatographic separations were performed over silica gel 70 (Aldrich Chemical Co.) to separate lactonic sophorolipid from the natural mixture. 50 g of silica gel was used to pack a glass column (5 cm×50 cm) in the eluent ($CHCl_3$/MeOH mixture). 200 ml of eluent was run through the column before the crude mixture (dissolved in a minimal volume of eluent) was loaded onto the top of the column matrix. Different fractions were subsequently eluted (1 mL/min). A lactonic fraction was collected separately and all other fractions were mixed to form non-lactonic sophorolipid mixture.

3. Synthesis of Open Ring Sophorolipid 10 g of natural mixture sophorolipids were stirred in 25 ml 4 N NaOH and refluxed for 30-60 minutes. After cooling, the mixture was acidified with diluted HCl to pH 4. Extraction was carried out with n-pentanol and the compound dried over $Na_2SO_4$. Solvent was removed in vacuo. Purification of the compound was performed with column chromatography as described in section 2 above.

4. Synthesis of Ethyl 17-L[(2'-O-β-D glucopyranosyl-β-D-glucopyranosyl)-oxy]-cis-9-octadecenoate 6',6"-diacetate Ethyl 17-L-[(2'-O-β-D-glucopyranosyl-β-D-glucopyranosyl)-oxy]-cis-9-octadecenoate was synthesized by adding 2 g of dry crude sophorolipid and 2.5 mL 0.021 N sodium ethoxide in methanol solution to a 100 mL round-bottomed flask equipped with a reflux condensor. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

The synthesized ethyl 17-L-[(2'-O-β-D-glucopyranosyl-β-D-glucopyranosyl)-oxy]-cis-9-octadecenoate (500 mg) was dissolved in 20 mL of dry tetrahydrofuran (THF). To this solution were added vinyl acetate (2 mL) and Novozym 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 490 mg of ethyl 17-L[(2'-O-β-D glucopyranosyl-β-D-glucopyranosyl)-oxy]-cis-9-octadecenoate 6',6"-diacetate.

The synthesis of other related compounds, such as methyl- and butyl-based compounds, etcetera, can be accomplished by substituting sodium methoxide or sodium butoxide, etcetera, respectively for the sodium ethoxide, resulting in sophorolipid methylester and sophorolipid butylester, etcetera, respectively. The amount of dry crude sophorolipid and the amount and normality of the sodium $(CH_2)_n$ oxide can be varied appropriately by those of ordinary skill in the art without undue experimentation.

5. Synthesis of Ethyl 17-L-[(2'-O-β-D-glucopyranosyl-β-D-glucopyranosyl)-oxy]-cis-9-octadecenoate-6"-acetate To a solution of ethyl ester, (325.4 mg) and vinyl acetate (230.9 µl) in dry THF (5 ml), lipase PS-C (100 mg) was added and stirred at 40° C. for 72 hr under nitrogen atmosphere. The enzyme was filtered out followed by washing with THF (3×3 ml). After removal of solvent the residue was subjected to silica gel column chromatography with MeOH/$CHCl_3$ (1:9, v/v) to afford the product.

The synthesis of other related compounds, such as methyl- and butyl-based compounds, etcetera, can be accomplished by substituting methyl ester or butyl ester, etcetera, respectively for the ethyl ester. The amount of vinyl acetate, THF and lipase can be varied appropriately by those of ordinary skill in the art without undue experimentation. Other types of suitable sophorolipids also can be synthesized by those of ordinary skill in the art without undue experimentation.

6. Synthesis of Hexyl 17-L[(2'-O-β-D glucopyranosyl-β-D-glucopyranosyl)-oxy]-cis-9-octadecenoate Hexyl 17-L-[(2'-O-β-D-glucopyranosyl-β-D-glucopyranosyl)-oxy]-cis-9-octadecenoate was synthesized by adding 2 g of dry crude sophorolipid and 2.5 mL 0.021 N sodium hexanoxide in hexanol solution to a 100 mL round-bottomed flask equipped with a reflux condensor. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

Other types of suitable sophorolipids also can be synthesized by those of ordinary skill in the art without undue experimentation.

7. Antifungal Assay

Sophorolipid solution was prepared by adding 15 mg of compound in 1 ml sucrose solution, pH 8.5.

All assay were carried out in 96 well plates using Yeast extract-Maltose medium. The logarithmic growing cultures were incubated with 5 mg/ml of sophorolipids for 48 hours at 30° C. Following incubation, the wells were measured for Optical Density (OD) at 400 nm using microtitre plate readers. Percent (%) inhibition of growth was calculated corresponding to the OD in control wells containing no sophorolipid.

8. Results and Discussion

As shown in Table 1, the ability of an effective amount of various forms of sophorolipids to inhibit the growth of an organism varies on the type of organism under test. Thus, the invention illustrates the use of natural, lactonic, open ring, ethyl ester, methyl ester, hexyl ester, 6'-acetate ethyl ester, 6',6"-diacetate ethyl ester sophorolipids as anti-fungal agents. These results can be extrapolated and serve as the basis for the use of sophorolipids as by those of ordinary skill in the art without undue experimentation. The applications of using sophorolipids in field of medicine, pesticides, food preservatives, media ingredient, etc., are tremendous, such as for treating various infections, as well as for other applications.

9. Additional Exemplary Compounds

Synthesis of Methyl 17-L-([2'-O-β-D-glucopyranosyl-β-D-glucopyranosyl]-oxy)-cis-9-octadecenoate (SL-Me, 1)

In a typical reaction, to a 100 mL round-bottomed flask equipped with a reflux condenser were added 10 g of dry crude sophorolipid and 10 mL 0.022 N sodium methoxide in methanol solution. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid methylester as a white solid. The precipitate was filtered, washed with ice water, and lyophilized, resulting in 8.77 g of product (yield 95.0%).

Synthesis of Ethyl 17-L-([2'-O-β-D-glucopyranosyl-β-D-glucopyranosyl]-oxy)-cis-9-octadecenoate (SL-Et, 2)

A procedure identical to the one described above for the methyl ester was used to prepare the sophorolipid ethyl ester. Crude sophorolipid (2 g) in 2.5 mL of 0.021 N sodium ethoxide in ethanol was refluxed for 3 hr. The identical workup as for analogue 1 gave 1.85 g of the ethyl ester (yield 85%).

Synthesis of Butyl 17-L-([2'-O-β-D-glucopyranosyl-β-D-glucopyranosyl]-oxy)-cis-9-octadecenoate (SL-Bu, 3)

Similarly to the synthesis of the methyl/ethyl esters, 2.5 mL of 0.038 N sodium butoxide in butanol and 2 g of the dry crude sophorolipid were added to a round-bottom flask fitted with a reflux condenser. The reaction mixture was stirred for 3 hr at 65° C. The usual workup procedures gave 1.5 g of the butyl ester (yield 51%).

Methyl 17-L-([2'-O-β-D-glucopyranosyl-β-D-glucopyranosyl]-oxy)-cis-9-octadecenoate 6',6''-diacrylate (4)

To a 50 mL round-bottom flask under dry argon were added 1 g of Novozyme 435 and a solution of 1 (500 mg) in 20 mL of dry THF. Excess of vinyl acrylate (2 mL) was then added to the reaction mixture, and the contents were stirred magnetically at 35° C. for 96 hr. The reaction setup was secluded from the light with black paper. The usual workup procedure led to the isolation of 0.51 g of the crude product. Product purification by column chromatography yielded 0.48 g (yield 87%) of 4.

Methyl 17-L-([2'-O-β-D-glucopyranosyl-β-D-glucopyranosyl]-oxy)-cis-9-octadecenoate 6',6''-diacetate (5)

Compound 1 (500 mg) was dissolved in 20 mL of dry THF. To this solution were added vinyl acetate (2 mL) and Novozyme 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 515 mg (yield 91%) of 5.

Ethyl 17-L-([2'-O-β-D-glucopyranosyl-β-D-glucopyranosyl]-oxy)-cis-9-octadecenoate 6',6''-diacetate (6)

Compound 2 (500 mg) was dissolved in 20 mL of dry THF. To this solution were added vinyl acetate (2 mL) and Novozyme 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 490 mg (yield 87%) of 6.

Butyl 17-L-([2'-O-β-D-glucopyranosyl-β-D-glucopyranosyl]-oxy)-cis-9-octadecenoate 6',6''-diacetate (7)

Compound 3 (500 mg) was dissolved in 20 mL of dry THF. To this solution were added vinyl acetate (2 mL) and Novozyme 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 483 mg (yield 86%) of 7.

Methyl 17-L-([2'-O-β-D-glucopyranosyl-β-D-glucopyranosyl]-oxy)-cis-9-octadecenoate 6',6''-disuccinate (8)

Compound 1 (500 mg) was dissolved in 20 mL of dry THF. To this solution were added succinic anhydride (2 mL) and Novozyme 435 (1 g), and the suspension was stirred magnetically at 35° C. for 96 hr. The enzyme was filtered off, the solvent was evaporated, and the product was purified by column chromatography (eluent $CHCl_3$/MeOH, 8:2) to give 492 mg (yield 75%) of 8.

Novozyme 435 catalyzed synthesis of 17-L-([2'-O-β-D-glucopyranosyl-β-D-glucopyranosyl]-oxy)-cis-9-octadecenoic acid 1',6''-lactone (Sophorolactone, 9)

For the following, an inert atmosphere was maintained using a glovebag and dry argon. To an oven dried 100 mL round-bottomed flask were transferred 1.5 g of methyl 17-L-([2'-O-β-D-glucopyranosyl-β-D-glucopyranosyl]-oxy)-cis-9-octadecenoate (1), 2.2 g of zeolite, 2 g of Novozyme 435 (dried in a vacuum desiccator, 0.1 mmHg, 25° C., 16 hr), and dry THF (50 mL), and the round-bottomed flask was immediately stoppered. The flask was then placed in a constant temperature oil bath maintained at 35° C. for 96 hr, and the contents were stirred magnetically. A control reaction was set up as described above except Novozyme 435 was not added. TLC($CHCl_3$/MeOH, 7:3) was used to follow the progress of the reaction. The reaction was quenched by removing the enzyme and zeolite by vacuum filtration (glass fritted filter, medium porosity), the enzyme was washed 3-4 times with 5 mL portions of THF, the filtrates were combined, and solvent was removed in vacuo to give 1.45 g of the product. The crude product (1.45 g) was purified by column chromatography over silica gel (100 g, 130-270 mesh, 60 Å, Aldrich) using a gradient solvent system of chloroform/methanol (2 mL/minute) with increasing order of polarity to give 1.2 g (yield 84%) of purified product.

17-L-([2'-O-β-D-glucopyranosyl-β-D-glucopyranosyl]-oxy)-cis-9-octadecenoic acid 1',6''-lactone 6'-acrylate (10)

To an oven-dried 100 mL round-bottomed flask were added 9 (1.0 g), 2.0 g of zeolite, and 3 g of Novozyme 435 that was dried (0.1 mmHg, 25° C., 16 hr). Then, dry THF (30 mL) was added, and the round-bottomed flask was immediately stoppered. Vinyl acrylate (2.5 mL) was added, and the round-bottomed flask was wrapped with black paper to seclude it from the light. This flask was then placed in a constant temperature oil bath (35° C.) with magnetic stirring for 96 hr. A control reaction was set up as was described above except that Novozyme 435 was not added. Progress of the reaction was followed by TLC($CHCl_3$/MeOH, 9:1). The reaction was quenched by removing the enzyme and zeolite by vacuum filtration (glass fritted filter, medium porosity), the enzyme was washed 3-4 times with 5 mL portions of THF, the filtrates were combined, and solvent was removed in vacuo to give 1.5 g of the product. The crude product (1.05 g) was purified by column chromatography over silica gel (50 g, 130-270 mesh, 60 Å, Aldrich) using a gradient solvent system of chloroform/ methanol (2 mL/minute) with increasing order of polarity to give 0.9 g (yield 83%) of purified product.

Synthesis of Ester Sophorolipid Derivatives.

The sophorolipid mixture was refluxed with an alcoholic solution of sodium methoxide to yield the methyl ester (SL-Me, 1). The optically active compound, $[\alpha]^{25}_D$-9.77, was isolated in 95% yield. The product was soluble in anhydrous THF and was identified on the basis of the results of a MALDI-TOF mass spectrum (m/z 659.85 (M+Na)$^+$) and detailed spectral data. This sophorolipid methyl ester was described earlier, but its complete spectral data was not given. The $^1$H NMR spectrum of 1 was complex, and chemical shifts were spread over the 1.2-5.5 ppm range. The acetyl group resonances observed around 2.2 ppm for the natural sophorolipid mixture were no longer seen, and the methyl ester group was a singlet at 3.68 ppm. The assignments shown were derived from a $^1$H-$^1$H COSY 45 NMR spectrum. The $^{13}$C NMR spectrum of 1 showed a signal corresponding to the methyl group at 50.99 ppm. The carbonyl group (C-1, Scheme 2) resonance was observed at 175.04 ppm. Assignments of the resonances in the $^{13}$C NMR spectrum were made on the basis of a $^1$H-$^{13}$C HETCOR experiment. By similarly reacting the natural sophorolipid mixture with sodium ethoxide (NaOC$_2$H$_5$) and sodium butoxide (NaOC$_4$H$_9$), the ester derivatives ethyl 17-L-([2'-O-β-D-glucopyranosyl-β-D-glucopyranosyl]-oxy)-cis-9-octadecenoate (SL-Et, 2) and butyl 17-L-([2'-O-β-D-glucopyranosyl-β-D-glucopyranosyl]-oxy)-cis-9-octadecenoate (SL-Bu, 3) were formed.

Enzyme Screening.

The SL-Me was next subjected to lipase-catalyzed esterification with vinyl acrylate in dry THF. A study to determine the efficiency of different lipases (PPL, CCL, PS-30, AK, MAP-10, Novozyme 435, and Lipozyme IM) for the acylation of 1 in dry organic solvent at room temperature was performed. In 48 hr, all lipases showed conversion, and the extent of conversion varied considerably with the source (PPL≈40%, CCL<30%, PS-30≈50%, AK≈50%, MAP-10<10%, and Novozyme 435>70%). Hence, Novozyme 435 was found to be the lipase of choice for the acylation with vinyl acrylate.

Lipase-Catalyzed Regioselective Acylations.

Initial attempts at the synthesis of the monoacryl sophorolipid derivative were conducted using excess vinyl acrylate and Novozyme 435 as the catalyst. The resulting product was purified by column chromatography over silica gel and was identified from its proton and carbon NMR spectra. The compound had an (M+Na)$^+$ ion peak at m/z 767.55 from MALDI-TOF, which is 43 mass units higher than that calculated for the monoacryl derivative. The proton NMR of the compound showed resonances at 5.92-6.44 ppm due to two acryl groups in the molecule. The proton NMR spectrum of the compound showed a downfield shift in the resonance positions of both the C-6' and C-6" protons. However, conclusive determination of the position of the acryl groups in the molecule was not possible from the proton NMR spectrum due to its complexity. The $^{13}$C NMR spectrum of this product was edited using a DEPT 135 pulse sequence to separate out the resonances due to the metheine and methyl carbons from those due to the methylene carbons. The DEPT 135 spectrum of the product clearly showed peaks due to two acryl groups (COCH=CH$_2$) at 129.79, 129.95, 130.63, and 130.75. The peaks due the metheine carbons appear inverted. Additionally, carbons C-9 and C-10 in the lipid chain of the molecule appeared at 129.79 and 129.95 ppm. Importantly, the resonances at 63.91 and 64.02 ppm for C-6' and C-6", respectively, were 2.0 ppm downfield compared to the corresponding methyl ester. Hence, these results suggest the formation of a diacryl product that is acylated at positions C-6' and C-6". Interestingly, it was observed that the resonance position of C-2' (carbon bearing no free hydroxyl group) was shifted downfield by ~2 ppm upon formation of the acyl ester at C-6' and C-6". This downfield shift in the resonance position of C-2' might very well be due to the conformational changes in the lipid structure upon acylation. Furthermore, an upfield shift of 2.5 ppm for the resonances corresponding to C-5' and C-5" and no significant changes in the resonance positions of the other carbons in the molecule were found. The upfield shift in the resonance positions of C-5' and C-5" is consistent with the γ-effect that is caused by the attachment of the acryl groups at the C-6' and C-6" hydroxyls. Therefore, these NMR results showed that the Novozyme 435 catalyzed acylation proceeded in a highly regioselective fashion where only the C-6' and C-6" hydroxyls in the molecule were acrylated. This product (4) was therefore conclusively identified as methyl 17-L-([2'-O-β-D-glucopyranosyl-β-D-glucopyranosyl]-oxy)-cis-9-octadecenoate 6',6"-diacrylate.

The above reaction was further extended to prepare other related 6',6"-diacylated derivatives:

Methyl 17-L-([2'-O-β-D-glucopyranosyl-β-D-glucopyranosyl]-oxy)-cis-9-octadecenoate 6',6"-diacetate (5) was prepared by the Novozyme 435 catalyzed acylation of methyl 17-L-([2'-O-β-D-glucopyranosyl-β-D-glucopyranosyl]-oxy)-cis-9-octa-decenoate (SL-Me, 1), using vinyl acetate in dry THF. Compound 5 was isolated by column chromatography over silica gel (m/z 744.22 (M+Na)$^+$, $[\alpha]^{25}_D$-7.22). The $^1$H NMR spectrum of 5 showed resonances similar to those of 1. The two acetyl groups appeared as a singlet at 2.08 (6H) ppm. In the $^{13}$C NMR spectrum, the resonances for the C-6' and C-6" protons were observed ~0.5 ppm downfield relative to 1. The DEPT 135 $^{13}$C NMR spectrum of 5 showed the presence of the two acetyl groups in the molecule (19.69 (double) ppm) and also confirmed the positions of acylation. The DEPT 135 spectrum of 5, when compared to that of 1, showed a downfield shift of about 2.0 ppm in the resonance position of C-6' and C-6" and an upfield shift of about 2.5 ppm in the resonance position of C-5' and C-5". Furthermore, except for the downfield shift of ~2 ppm in the resonance position of C-2', there were no observable changes in the resonance position of the other carbons in the molecule. Hence, it was concluded that the acetylation of 1 with vinyl acetate catalyzed by the lipase Novozyme 435 was highly regioselective.

Acetylation of SL-Et (2) and SL-Bu (3) with vinyl acetate in dry THF catalyzed by Novozyme 435 also led to the formation of ethyl 17-L-([2'-O-β-D-glucopyranosyl-β-D-glucopyranosyl]-oxy)-cis-9-octadecenoate 6',6"-diacetate (6, m/z 757.36 (M+Na)$^+$, $[\alpha]^{25}_D$-2.11 (c=0.0121 g/mL)) and butyl 17-L-([2'-O-β-D-glucopyranosyl-β-D-glucopyranosyl]-oxy)-cis-9-octadecenoate 6',6"-diacetate (7, m/z 786.46 (M+Na)$^+$, $[\alpha]^{25}_D$-1.63 (c=0.0183 g/mL)) in a regioselective fashion. Spectral data for 6 and 7 were similar to that observed for 5 with additional resonances that correspond to the ester alkyl group. The DEPT 135 spectra of 6 and 7, when compared to that of 1, also showed a downfield shift of about 2.0 ppm in the resonance position of C-6' and C-6" and an upfield shift of about 2.5 ppm in the resonance position of C-5' and C-5".

The preparation of regioselectively modified sophorolipids that contain carboxyl functionalities is of interest. Hence, the acylation of 1 as above was conducted using succinic anhydride as the acylating agent to prepare methyl 17-L-([2'-O—β-D-glucopyranosyl-β-D-glucopyranosyl]-oxy)-cis-9-octa-decenoate 6',6"-disuccinate (8). Compound 8 was purified by column chromatography, which gave a viscous colorless liquid (m/z 861.29 (M+Na)$^+$, $[\alpha]^{25}_D$-3.57). In the $^1$H NMR spectrum of 8, the methylene protons of the succinate groups appeared at 2.50 (8H) ppm. Also, the resonances for the C-6' and C-6" protons were shifted downfield (~0.5 ppm) from those observed in 1. The assignment of the resonances in the $^1$H NMR spectrum was made from a $^1$H-$^1$H COSY 45 experiment performed on 8. The position of the succinate groups at C-6' and C-6" was established from the DEPT 135 $^{13}$C NMR spectrum. When compared to the DEPT 135 $^{13}$C NMR spectrum of 1, the resonances for the C-6' and C-6" in 8 were shifted downfield by about 2.0 ppm and resonances for the C-5' and C-5" were shifted upfield by 2.5 ppm. The observed NMR studies established that succinylation of the C-6' and C-6" hydroxyl groups did indeed occurred regioselectively.

Synthesis of Sophorolactone.

One of the objectives of this invention is the site-selective synthesis of a monoacryl derivative of 1. Such a product could be used as a glycolipid monomer that is polymerizable to linear chains through well-established free radical methods. For this purpose, reactions of 1 were conducted where the ratio of 1 to vinyl acrylate was varied. When the ratio of 1 to vinyl acrylate was 1:1 or less, 9 ($[\alpha]^{25}_D$-4.25, m/z 627.95 (M+Na)$^+$) was formed. Compound 9 was separated from the unreacted SL-Me by column chromatography. Comparison of the $^1$H NMR spectra for 9 and 1 showed substantial differences in the appearance of the proton signals in the 3.25-4.5 ppm region that are due to carbohydrate protons. Assignments to resonances were made from a $^1$H-$^1$H COSY NMR spectrum. The two doublets assigned to H-1' and -1" at 4.49 and 4.52, respectively, were shifted so that they are in closer proximity for 1 than for 9. Furthermore, the $^1$H NMR spectrum of 9 did not indicate that acrylation occurred and had no resonances corresponding to the methyl ester. These anomalous features of the $^1$H NMR spectrum of 9 suggested the formation of a lactone where the ester linkage was between the carboxylic acid end group of the fatty acid chain and one of the hydroxyl groups of the sophorose ring. The $^1$H NMR spectrum of 9 also showed a 0.5 ppm downfield shift in the resonance position of the C-6" protons, suggesting participation of the C-6" hydroxyl group in the formation of the lactone ring. However, conclusive determination of the hydroxyl group(s) on the sophorose moiety that took part in lactone formation required additional studies by $^{13}$C NMR. Specifically, the $^{13}$C NMR of 9 was recorded after editing by the DEPT 135 pulse sequence. This permitted resolution of the resonances due to the methyl, methylene, and metheine carbons. The DEPT 135 spectra of 1 and 9 were compared. A downfield shift of 1.5 ppm in the resonance position of the C-6" was accompanied by an upfield shift of 1.3 ppm in the resonance position of the C-5". This observation confirmed that a bond between the hydroxyl of C-6" and the lipid carbonyl carbon formed the lactone ester.

The structure of the lactone 9 is very interesting, as it is an unnatural analogue of the microbially produced macrolactone. The lactone 9 differs in the site at which the sophorose ring is attached to the fatty acid. Specifically, in 9, unlike the natural sophorolipids, the fatty acid carboxyl carbon (C-1) is linked to the C-6" hydroxyl, not to the C-4" hydroxyl. A structure has been proposed based on the lactonic structure 9 for a diacetyl sophorolipid isolated from a strain of *Torulopsis gropengiesseri*. The structure was proposed to be a 1,6"-lactone having acetate groups at the hydroxyls of C-6' and C-3". However, when the same compound was isolated, after detailed analysis, the structure of the compound was instead SL$_1$.

The successful synthesis of 9 provided a sophorolipid analogue that had only one primary hydroxyl group. Hence, this compound was an excellent candidate for the regioselective conversion of 9 to the corresponding monoacryl derivative linked only to the one remaining primary site. Indeed, the reaction of 9 with vinyl acrylate catalyzed by Novozyme 435 in dry THF gave 10 ($[\alpha]^{25}_D$-2.81, m/z 681.90 (M+Na)$^+$). The $^1$H NMR spectrum of 10 confirmed that the monoacrylation did indeed take place: 5.92 (1H, dd), 6.25 (1H, dd), and 6.44 (1H, dd). In addition, when compared to the $^1$H NMR spectrum of 9, the resonance position of the methylene on carbon 6' for 10 showed a 0.7 ppm downfield shift. Further proof of the acrylation position for 10 was obtained by comparison of the $^{13}$C DEPT 135 NMR spectra for 9 and 10. The spectrum of 10 showed a downfield shift of 2.0 ppm in the resonance position of the C-6' carbon and an upfield shift of 2.5 ppm in the resonance position of the C-5'.

Ethyl 17-L-[(2'-O-β-D-glucopyranosyl-β-D-glucopyranosyl)-oxy]-cis-9-octadecenoate-6'-acetate (11)

To a solution of ethyl ester (325.4 mg, 0.5 mmol), prepared from sophorolipid mixture disclosed above, and vinyl acetate (230.9 μl, 2.5 mmol) in dry THF (5 ml) Novozyme 435 (100 mg) was added and stirred at 40° C. for 2.5 hr under nitrogen atmosphere. The enzyme was filtered out followed by washing with THF (3×3 ml). After the removal of solvent, the residue was charged to a silica gel column chromatography with MeOH/CHCl$_3$ (1:24 to 2:23, v/v) to afford diacetate (33.0 mg, 9%) and monoacetate, 11 as white solid (267.0 mg, 77%).

Ethyl 17-L-[(2'-O-β-D-glucopyranosyl-β-D-glucopyranosyl)-oxy]-cis-9-octadecenoate-6"-acetate (12)

To a solution of ethyl ester (325.4 mg, 0.5 mmol) and vinyl acetate (230.9 μl, 2.5 mmol) in dry THF (5 ml), Lipase PS-C (100 mg) was added and stirred at 40° C. for 72 hr under nitrogen atmosphere. The enzyme was filtered out followed by washing with THF (3×3 ml). After removal of solvent the residue was subjected to silica gel column chromatography with MeOH/CHCl$_3$ (1:9, v/v) to afford amide 12 as a white solid (308 mg, 89%).

Ethyl 17-L-[(2'-O-β-D-glucopyranosyl-β-D-glucopyranosyl)-oxy]-cis-9-octadecenoate-6"-methacrylate (13)

To a solution of ethyl ester (325.4 mg, 0.5 mmol) and vinyl methacrylate (230.9 μl, 2.5 mmol) in dry THF (8 ml) Lipase PS-C (100 mg) was added and stirred at 40° C. for 72 hr under nitrogen atmosphere. The enzyme was filtered out followed by washing with THF (3×3 ml). After the removal of solvent the residue was subjected to silica gel column chromatography with MeOH/CHCl$_3$ (2:23, v/v) to afford 13 as white solid (318 mg, 86%).

p-Hydroxy phenethyl 17-L-[(2'-O-β-D-glucopyranosyl-β-D-glucopyranosyl)-oxy]-cis-9-octadecenamide (14)

To a solution of ethyl ester (325.4 mg, 0.5 mmol) and tyramine (69.9 mg, 0.51 mmol) in dry THF (5 ml) Novozyme 435 (100 mg) was added and stirred at 50° C. for 24 hr under nitrogen atmosphere. The enzyme was filtered out followed by washing with THF (3×3 ml). After the removal of solvent the residue was subjected to silica gel column chromatography with MeOH/CHCl$_3$ (1:9, v/v) to afford amide 14 as white solid (341.3 mg, 92%).

Phenethyl 17-L-[(2'-O-β-D-glucopyranosyl-β-D-glucopyranosyl)-oxy]-cis-9-octadecenamide (15)

To a solution of ethyl ester (325.4 mg, 0.5 mmol) and phenethylamine (64.0 µl, 0.51 mmol) in dry THF (5 ml) Novozyme 435 (100 mg) was added and stirred at 50° C. for 24 hr under nitrogen atmosphere. The enzyme was filtered out followed by washing with THF (3×3 ml). After the removal of solvent the residue was subjected to silica gel column chromatography with MeOH/CHCl$_3$ (1:9, v/v) to afford amide 15 as White solid (327 mg, 90%).

p-(tolyl)ethyl 17-L-[(2'-O-β-D-glucopyranosyl-β-D-glucopyranosyl)-oxy]-cis-9-octadecenamide (16)

To a solution of ethyl ester (325.4 mg, 0.5 mmol) and p-(tolyl)ethylamine (74.1 µl, 0.51 mmol) in dry THF (5 ml) was added Novozyme 435 (100 mg) and stirred at 50° C. for 24 hr under nitrogen atmosphere. The enzyme was filtered out followed by washing with THF (3×3 ml). After the removal of solvent the residue was subjected to silica gel column chromatography with MeOH/CHCl$_3$ (1:9, v/v) to afford amide 16 as white solid (340.4 mg, 92%).

p-Methoxyphenethyl 17-L-[(2'-O-β-D-glucopyranosyl-β-D-glucopyranosyl)-oxy]-cis-9-octadecenamide (17)

To a solution of ethyl ester (325.4 mg, 0.5 mmol) and p-methoxyphenethylamine (74.6 µl, 0.51 mmol) in dry THF (5 ml) Novozyme 435 (100 mg) was added and stirred at 50° C. for 24 hr under nitrogen atmosphere. The enzyme was filtered out followed by washing with THF (3×3 ml). After the removal of solvent the residue was subjected to silica gel column chromatography with MeOH/CHCl$_3$ (1:9, v/v) to afford amide 17 as white solid (351.5 mg, 93%).

p-Fluorophenethyl 17-L-[(2'-O-β-D-glucopyranosyl-β-D-glucopyranosyl)-oxy]-cis-9-octadecenamide (18)

To a solution of ethyl ester (325.4 mg, 0.5 mmol) and p-fluorophenethylamine (66.9 µl, 0.51 mmol) in dry THF (5 ml) Novozyme 435 (100 mg) was added and stirred at 50° C. for 24 hr under nitrogen atmosphere. The enzyme was filtered out followed by washing with THF (3×3 ml). After the removal of solvent the residue was subjected to silica gel column chromatography with MeOH/CHCl$_3$ (1:9, v/v) to afford amide 18 as white solid (331 mg, 89%).

p-Hydroxy phenethyl 17-L-[(2'-O-β-D-glucopyranosyl-β-D-glucopyranosyl)-oxy]-cis-9-octadecenamide-6',6"-diacetate (19)

To a solution of 14 (325.4 mg, 0.5 mmol) and vinyl acetate (369.5 µl, 4 mmol) in dry THF (5 ml) Novozyme 435 (115 mg) was added and the reaction mixture was stirred at 50° C. for 80 hr under nitrogen atmosphere. The enzyme was filtered out followed by washing of enzyme with THF (3×3 ml). After the removal of solvent residue was subjected to silica gel chromatography with MeOH/CHCl$_3$ (1:24, v/v) as eluent to afford 19 as white solid (375.8 mg, 91%).

p-Hydroxy phenethyl 17-L-[(2'-O-β-D-glucopyranosyl-β-D-glucopyranosyl)-oxy]-cis-9-octadecenamide-6',6"-dimethacrylate (20)

To a solution of 14 (325.4 mg, 0.5 mmol) and vinyl methacrylate (480.7 µl, 4 mmol) in dry THF (5 ml) Novozyme 435 (130 mg) was added and the reaction mixture was stirred at 50° C. for 80 hr under nitrogen atmosphere. The enzyme was filtered out followed by washing of enzyme with THF (3×3 ml). After the removal of solvent residue was subjected to silica gel chromatography with MeOH/CHCl$_3$ (1:24, v/v) as eluent to afford 20 as white solid (395.1 mg, 90%).

One-pot synthesis of 20 from ethyl ester: To a solution of ethyl ester (325.4 mg, 0.5 mmol) and tyramine (69.9 mg, 0.51 mmol) in dry THF (5 ml) was added Novozyme 435 (230 mg) and stirred at 50° C. for 24 hr. After addition of vinyl methacrylate (480.7 µl, 4 mmol) in dry THF (2 ml), the whole reaction mixture was stirred at 50° C. for next 80 hr. The enzyme was filtered out followed by washing of enzyme with THF (4×3 ml). After removal of solvent, the residue was subjected to silica gel chromatography with MeOH/CHCl$_3$ (1:24, v/v) as eluent to afford pure 20 as white solid (386 mg, 88%).

p-Hydroxy phenethyl 17-L-[(2'-O-β-D-glucopyranosyl-β-D-glucopyranosyl)-oxy]-cis-9-octadecenamide-6'-acetate (21)

To a solution of 14 (100.2 mg, 0.135 mmol) and vinyl acetate (61.9 µl, 0.67 mmol) in dry THF (5 ml) Novozyme 435 (35 mg) was added and the reaction mixture was stirred at 40° C. for 20 hr under nitrogen atmosphere. The enzyme was filtered out followed by washing of enzyme with THF (3×3 ml). After the removal of solvent, residue was subjected to silica gel chromatography with MeOH/CHCl$_3$ (1:24 to 2:23, v/v) as eluent to afford 20 (8.3 mg, 7%) and 21 as white solid (87.8 mg, 83%).

p-Hydroxy phenethyl 17-L-[(2'-O-β-D-glucopyranosyl-β-D-glucopyranosyl)-oxy]-cis-9-octadecenamide-6'-methacrylate (22)

To a solution of 14 (100.2 mg, 0.135 mmol), vinyl methacrylate (80.5 µl, 0.67 mmol) in dry THF (5 ml) Novozyme 435 (35 mg) was added and reaction mixture was stirred for 20 hr under nitrogen atmosphere. Then enzyme was filtered out and washed with THF (3×3 ml). The solvent was removed under vacuum and the residue was subjected to column chromatography on silica gel with MeOH/CHCl$_3$ (1:24 to 2:23, v/v) to afford 20 (7.1 mg, 6%) and 22 as white solid (87.5 mg, 80%).

p-Hydroxy phenethyl 17-L-[(2'-O-β-D-glucopyranosyl-β-D-glucopyranosyl)-oxy]-cis-9-octadecenamide-6"-acetate (23)

To a solution of 14 (100.2 mg, 0.135 mmol) and vinyl acetate (41.6 µl, 0.45 mmol) in dry THF (5 ml) Lipase PS-C (35 mg) was added and the reaction mixture was stirred at 40° C. for 72 hr under nitrogen atmosphere. The enzyme was filtered out followed by washing of enzyme with THF (3×3 ml). After the removal of solvent residue was subjected to silica gel chromatography with MeOH/CHCl$_3$ (2:23, v/v) as eluent to afford 23 as white solid (92.1 mg, 87%).

p-Hydroxy phenethyl 17-L-[(2'-O-β-D-glucopyranosyl-β-D-glucopyranosyl)-oxy]-cis-9-octadecenamide-6"-methacrylate (24)

To a solution of 14 (100.2 mg, 0.135 mmol), vinyl methacrylate (54.1 µl, 0.45 mmol) in dry THF (5 ml) Lipase PS-C (35 mg) was added and reaction mixture was stirred for 72 hr under nitrogen atmosphere. Then enzyme was filtered out and washed with THF (3×3 ml). The solvent was removed under vacuum and the residue was subjected to column chromatography on silica gel with MeOH/CHCl$_3$ (2:23, v/v) to afford 24 as white solid (96.2 mg, 88%).

The sophorolipid mixture produced by the fermentation of *C. bombicola* on glucose/oleic acid mixtures contains at least eight components that exist mainly in the lactonic and acidic forms. These compounds also have variable degrees of acetylation at the primary hydroxyl groups at 6'- and 6"-positions. To gain improved precision of group placement during sophorolipid acetylation reactions, an attempt to monoacylate without ethyl ester concurrent formation of the unnatural sophorolipid macrolactone esterified at the 6"-hydroxyl position was made. In addition, the feasibility of using mild lipase-catalysis to convert ethyl ester to a family of secondary amide sophorolipid analogs was investigated. Furthermore, the monoacylation and diacylation of sophorolipid amides were also studied.

The sophorolipid ethyl ester, which was obtained by treating the microbial sophorolipid mixture with sodium ethoxide, was used as a synthon for enzyme-mediated transformations to form corresponding sophorolipid monoacetate, amide, and other monoacyl and diacyl derivatives. Monoacylation of ethyl ester at the 6'-position to form analog 11, amidation of ethyl ester with primary amines (tyramine, phenethylamine, 2-(p-tolyl)ethylamine, p-methoxyphenethylamine, p-fluorophenethylamine) to form analogs 14-18, diacylation of amide 14 at the 6'- and 6"-positions to form 19 (from vinyl acetate) and 20 (from vinyl methacrylate), and monoacylation of amide 14 at the 6'-position to form 21 (from vinyl acetate) and 22 (from vinyl methacrylate) were all effectively catalyzed by a physically immobilized form of *Candida antartica* lipase B (Novozyme 435). To perform monoacylation reactions at the 6"-position of ethyl ester and amide 14, Lipase PS-C (lipase PS on Ceramic support) was used in place of Novozyme 435 to give 12-13, and 23-24, respectively. Attempts to prepare amides by chemical methods (e.g. by treatment of substrate with amines in dry THF at 40-60° C., refluxing the substrate and amine mixture in ethanol at 80° C. for 10 days) failed.

Synthesis of Sophorolipid Ethyl Ester.

The preparation and thorough structural elucidation (using $^1$H, $^{13}$C NMR, DEPT, $^1$H-$^1$H COSY, HETCOR, IR and Mass spectra) of ethyl ester was disclosed above.

Novozym 435 Catalyzed Monoacylation of Sophorolipid Ethyl Ester at the 6'-Position.

The diacylation of ethyl ester 1 at the 6'- and 6"-positions is disclosed above. In order to further improve the ability to precisely control the degree and site of modification of sophorolipid analogs, studies were carried out to prepare monoacylated derivatives from ethyl ester. Ethyl ester was treated with excess vinyl acetate in dry THF at 40° C. for 2.5 hr using Novozyme 435 as the catalyst. By this method, monoacetate 11 modified at the 6-position was formed in 77% yield. Also, a small amount (9%) of the corresponding diacetate modified at both the 6'- and 6"-positions was found. The optically active 11 ($[\alpha]^{25}_D$-10.80) was identified by an LC-APCI mass spectrum (m/z 715.51 [M+Na]$^+$ and 693.52 [M+H]$^+$), and detailed NMR spectral analyses. The appearance in $^1$H-NMR of additional resonances at 1.90-2.18 ppm (m) for three protons, and the downfield shift of two protons of ethyl ester at 3.20-3.95 ppm (m) to 4.21 (1H, m) and 4.39 (1H, m) for 11, showed the presence of one acetyl group in the molecule. $^{13}$C NMR of 11 showed a downfield shift of ~2 ppm in C-6' (65.06 ppm) as compared to that for ethyl ester (63.24 ppm). Also, there was no significant change in C-6". The occurrence of monoacetylation at C-6' was further supported by $^{13}$C-NMR resonances at 21.08 and 172.72 ppm corresponding to the acetyl CH$_3$ and C=O, respectively. Monoacetylation at C-6' also resulted in an upfield shift of ~2 ppm of C-5' which is explained by the γ-effect between C-5' and the neighboring acetyl C=O atom. A downfield shift of ~2 ppm in C-2' (carbon bearing no free hydroxyl group) from 81.85 ppm in ethyl ester to 84.00 ppm in 11, was also observed which might be associated with a conformational change upon acetylation at C-6'. The assignment of protons and carbons were made by comparison of $^1$H and $^{13}$C signals of precursor ethyl ester with 11, and by careful inspection of the $^1$H-$^1$H COSY, $^1$H-$^{13}$C HETCOR spectra of 11. Metheine, methylene and methyl groups were distinguished by a $^{13}$C NMR DEPT spectrum of the molecule. The resonances in the $^1$H NMR of 11 at 5.35 ppm (m) for two protons were due to H-9 and H-10. These assignments were further supported by $^{13}$C peaks at 130.91 and 131.04 corresponding to C-9 and C-10. Thus, these results showed that Novozyme 435 was an effective catalyst for the monoacylation of ethyl ester at C-6'- and 11 was identified as ethyl 17-L-[(2'-O-β-D-glucopyranosyl-β-D-glucopyranosyl)-oxy]-cis-9-octadecenoate-6'-acetate.

Lipase PS-C Catalyzed Regioselective Monoacylation of the Sophorolipid Ethyl Ester 1 at C-6".

Ethyl ester was treated at 40° C. for 72 hr with an excess of vinyl acetate in dry THF using Lipase PS on a ceramic support (Lipase PS-C). This gave monoacetate 12, selectively modified at C-6", in 89% yield. 12 ($[\alpha]^{25}_D$-9.67) was identified by an LC-APCI mass spectrum (m/z 715.51 [M+Na]$^+$) and detailed NMR spectral analyses. The appearance in the $^1$H-NMR for 12 of additional resonances at 1.90-2.18 ppm for three protons, and the downfield shift of two protons of ethyl ester at 3.20-3.95 ppm to 4.20 (1H) and 4.37 (1H) for 12, showed the presence of one acetyl group in the molecule. The $^{13}$C NMR of 12 when compared to ethyl ester showed a downfield shift of ~2 ppm in C-6" (62.77 to 64.87 ppm). Also, there was no significant change in the peak position of C-6'. The occurrence of monoacetylation at C-6" was further supported by $^{13}$C-NMR resonances at 20.88 and 172.73 ppm corresponding to the acetyl CH$_3$ and C=O, respectively. Monoacetylation at C-6" also resulted in an upfield shift of ~2 ppm for C-5" which is due to the γ-effect (see above). The assignment of protons and carbons were made by comparison of $^1$H and $^{13}$C signals of precursor ethyl ester with 12, and by careful inspection of the $^1$H-$^1$H COSY, $^1$H-$^{13}$C HETCOR spectra of 12. Metheine, methylene and methyl groups were distinguished by a $^{13}$C NMR DEPT spectrum of the molecule. No significant changes were observed for ethyl ester, 11, and 12 in the positions of protons and carbons associated with the sophorolipid fatty acid CH=CH moiety. Also, to further substantiate the difference in the NMR spectra of 11 and 12, they were mixed in equimolar amounts. Study of the $^{13}$C DEPT 135 of this mixture showed distinctly resolved signals for 11 at 65.06 (C-6'), 62.78 (C-6") and C-2' (84.00), and for 12 at 63.23 (C-6') 64.87 (C-6") and C-2' (81.84). Thus, 12 was identified as ethyl 17-L-[(2'-O-β-D-glucopyranosyl-β-D-glucopyranosyl)-oxy]-cis-9-octadecenoate-6"-acetate. Thus, these results showed that Lipase PS-C was an effective catalyst for the acetylation of ethyl ester at C-6".

The above reaction was further extended to the preparation of the related monomethacrylate derivative. The Lipase-PS-C-mediated acryloylation of ethyl ester using excess of vinyl methacrylate in dry THF at 40° C. in 72 hr afforded ethyl 17-L-[(2'-O-β-D-glucopyranosyl-β-D-glucopyranosyl)-oxy]-cis-9-octadecenamide-6"-methacrylate 13 ($[\alpha]^{25}_D$-5.67; m/z 741.52 [M+Na]$^+$) in 86% yield. This compound had $^1$H NMR resonances similar to 12 except those that appeared at 1.93 (s), 5.63(s), and 6.11(s) ppm in 13 due to replacement of an acetyl group in 12 by a methacryl group at C-6". The resonances in the $^{13}$C NMR spectrum of 13 at 18.56, 126.43, 137.85, and 168.67 ppm further support the presence of a methacryl moiety in the molecule. Moreover, the $^{13}$C NMR showed a significant downfield shift for C-6" (from 62.77 ppm in ethyl ester to 65.15 ppm in 13), an upfield shift for the C-5"-signal, and no change for C-2'. Therefore, it was concluded that lipase PS-C is an excellent catalyst for highly regioselective acylation of ethyl ester at C-6" using vinyl acetate or vinyl methacrylate.

Enzyme Screening for Amidation Reaction.

For amidation of ethyl ester with primary amines (tyramine, phenethylamine, p-methoxyphenethylamine, 2-(p-tolyl)ethylamine, p-fluorophenethylamine), different lipases (PPL, CCL, PS-30, AK, MAP-10, Novozyme 435, and Lipozyme IM) in dry organic solvent at different temperatures (room temperature, 30°, 40° and 50° C.) were evaluated. Only Novozyme 435 was able to catalyze the formation of amide in high yield. A preferable condition for the reaction was in dry THF at 50° C. for 24 hr. Amidation did not occur when the lipases other than Novozyme 435 were used.

Novozyme 435 Catalyzed Amidation of Sophorolipid Ethyl Ester.

Novozyme 435 was used to catalyze mild amidation reactions between primary amines (tyramine, phenethylamine, p-methoxyphenethylamine, 2-(p-tolyl)ethylamine, p-fluorophenethylamine) and the sophorolipid ethyl ester. When tyramine was used, the secondary amide 14 ($[\alpha]^{25}_D$-12.33) was formed in 92% yield (Scheme 1). 14 was purified by column chromatography over silica gel with methanol/chloroform (1:9, v/v) as eluent. Study of the LC-APCI mass spectrum of 14 showed an ion peak at 742.27 ([M+H]$^+$). The $^1$H NMR spectrum of 14 showed the absence of resonances for O—CH$_2$CH$_3$ of ethyl ester. Instead, protons corresponding to the tyramine amide moiety at 2.68 ppm ([C=O]HNCH$_2$CH$_2$, t), 3.20-3.72 ppm ([C=O]HNCH$_2$CH$_2$, m), and the aromatic region at 6.71 ppm (2H, d, J=6.71 Hz) and 7.01 ppm (2H, d, J=6.71 Hz) were found. Similarly, the $^{13}$C NMR spectrum of 14 showed the absence of resonances for O—CH$_2$CH$_3$ of ethyl ester. Instead, carbons corresponding to the tyramine amide moiety were found at positions that correspond with the expected product structure. IR analysis of 14 showed an absorption peak at 1643 cm$^{-1}$ that corresponds to the amide-I band of the NH—C=O group. The retention of the disaccharide structure for 14 was evident by study of the sugar ring protons and carbons. For example, the acetal carbons C-1' and C-1" showed signals at 102.82 and 104.75 ppm that are consistent with that expected based on comparisons to ethyl ester. Representative $^{13}$C and $^1$H NMR signals for the fatty acid moiety of 14 were also observed. For example, resonances in the $^1$H NMR of 14 corresponding to the CH=CH moiety at 5.35 ppm (2H, m) are due to H-9 and H-10. Also, in the $^{13}$C NMR spectrum, resonances at 130.94 and 131.00 due to C-9 and C-10, respectively, were observed. Furthermore, the $^{13}$C resonance of the (C=O)—NH group was observed at 176.35 ppm. Based on these results and other spectral observations, 14 was identified as p-hydroxy phenethyl 17-L-[(2'-O-β-D-glucopyranosyl-β-D-glucopyranosyl)-oxy]-cis-9-octadecenamide). Thus, it was concluded that Novozyme 435 catalyzed the amidation of ethyl ester with tyramine to give 14.

With a view to establish a general method for amide preparation, the above reaction was extended to prepare other related sophorolipid amide derivatives. Phenethyl 17-L-[(2'-O-β-D-glucopyranosyl-β-D-glucopyranosyl)-oxy]-cis-9-octadecenamide 15 was synthesized by the Novozyme 435-catalyzed amidation of ethyl ester with phenethylamine in dry THF at 50° C. The resulting product 15 was purified by column chromatography over silica gel with methanol/chloroform (1:9, v/v) as eluent with high yield (90%). This optically active compound ($[\alpha]^{25}_D$-13.93) showed 748.72 [M+Na]$^+$ and 726.72 [M+H]$^+$ ions peaks in the LC-APCI mass spectrum. The $^1$H NMR of the product did not have resonances corresponding to the —OCH$_2$CH$_3$ group for ethyl ester. Instead, proton resonances at 2.78 ppm (2H, t), an additional two protons (compared to that of ethyl ester) in the region 3.20-3.72 ppm (m), and five protons in the aromatic region at 7.15-7.30 ppm (m) showed that the —COOCH$_2$CH$_3$ moiety in precursor ethyl ester had been replaced with the —CONH(CH$_2$)$_2$C$_6$H$_5$ moiety of amide 15. The presence of this moiety was further confirmed by the $^{13}$C NMR spectrum that showed peaks at 36.65, 41.98, 127.42, 129.56, 129.93, 140.61 and 176.32 ((C=O)NH). The presence of the amide linkage was consistent with the IR band at 1638 cm$^{-1}$. Methylene and metheine carbons were distinguished by a DEPT experiment. The $^1$H and $^{13}$C NMR for rest part of the molecule were similar to those of ethyl ester or 14.

The above reaction was further extended to the preparation of p-(tolyl)ethyl 17-L-[(2'-O-β-D-glucopyranosyl-β-D-glucopyranosyl)-oxy]-cis-9-octadecenamide (16, m/z 762.77 [M+Na]$^+$ and 740.78 [M+H]$^+$, $[\alpha]^{25}_D$-11.20), p-methoxyphenethyl 17-L-[(2'-O-β-D-glucopyranosyl-β-D-glucopyranosyl)-oxy]-cis-9-octadecenamide (17, m/z 756.47 [M+H]$^+$, $[\alpha]^{25}_D$-13.00), and p-fluorophenethyl 17-L-[(2'-O-β-D-glucopyranosyl-β-D-glucopyranosyl)-oxy]-cis-9-octadecenamide (18, m/z 766.75 [M+Na]$^+$, 744.76 [M+H]$^+$, $[\alpha]^{25}_D$-12.27) by Novozyme 435-catalyzed amidation of ethyl ester with p-(tolyl)ethylamine, p-methoxyphenethylamine and p-fluorophenethylamine, respectively, in dry THF at 50° C. Spectral data for 16, 17, and 18 were identical with that observed for ethyl ester with additional resonances that appeared due to replacement of —OCH$_2$CH$_3$ group by —NH(CH$_2$)$_2$C$_6$H$_4$—CH$_3$, —NH(CH$_2$)$_2$C$_6$H$_4$OCH$_3$ and —NH(CH$_2$)$_2$C$_6$H$_4$F groups, respectively. Namely, p-(tolyl)ethyl 17-L-[(2'-O-β-D-glucopyranosyl-β-D-glucopyranosyl)-oxy]-cis-9-octadecenamide (16) had additional resonances at 2.28 (3H, s, CH$_3$), 2.73 (2H, t, J=7.4 Hz, NCH$_2$CH$_2$), 3.20-3.77 (12H, m, NCH$_2$, H-2'-5', H-2"-5", H-6'$_a$ and -6"$_a$), and at 7.08 (4H, m, 4×Ar—H) due to appearance of —NH(CH$_2$)$_2$C$_6$H$_4$—CH$_3$. The presence of this moiety was further supported by $^{13}$C NMR peaks at 20.57, 35.38, 128.45, 128.79, 134.85, 136.40 and 171.99 ((C=O)NH). The presence of the —NH(CH$_2$)$_2$C$_6$H$_4$OCH$_3$ moiety for 17 was confirmed by the presence of $^1$H NMR resonances at 2.28 (3H, s, CH$_3$), 2.73 (2H, t, J=7.4 Hz, NCH$_2$CH$_2$), 3.20-3.77 (12H, m, NCH$_2$, H-2'-5', H-2"-5", H-6'$_a$ and -6"$_a$), and 3.75 (3H, s, OCH$_3$), 6.83 (2H, d, J=8.5 Hz, 2×Ar—H), and 7.11 (2H, d, J=8.5 Hz, 2×Ar—H), and carbon resonances at 35.81, 42.20, 55.85 (OCH$_3$), 115.07, 130.90, 132.65, 159.89 and 176.41([C=O]NH). p-Fluorophenethyl 17-L-[(2'-O-β-D-glucopyranosyl-β-D-glucopyranosyl)-oxy]-cis-9-octadecenamide (18) showed resonances in the $^1$H NMR at 2.77 (2H, t, J=7.4 Hz, NCH$_2$CH$_2$), 3.22-3.72 (12H, m, NCH$_2$ together with H-2'-5', H-2"-5", H-6'$_a$ and -6"$_a$), 6.93-7.02 (2H, m, 2×Ar—H) 7.17-7.25 (2H, m, 2×Ar—H). The presence of —NH(CH$_2$)$_2$C$_6$H$_4$F was further supported by the observation of $^{13}$C NMR peaks at 35.41, 39.95, 114.71, 114.98, 130.30, 130.62, 135.65, 159.20, 162.39. Hence, Novozyme 435 was found to be an excellent catalyst for the synthesis of secondary amides from reactions between ethyl ester with primary amines.

Novozyme 435-Catalyzed Diacylation (at 6' and 6"-Positions) of 14.

To further extend the level of structural control attainable with the new sophorolipid amides described herein, the diacylation of sophorolipid amide 14 was studied. 14 was treated with excess vinyl acetate in dry THF at 50° C. for 80 hr using Novozyme-435 as catalyst. By this method, the corresponding diacetyl derivative 19 in high yield (91%) was formed. The optically active product 19 ($[\alpha]^{25}_D$-6.27) was identified by an LC-APCI mass spectrum. The spectrum gave m/z 826.56 [M+H]$^+$, which is 82 mass units higher then 14 that corresponds to the addition of two acetyl groups. The $^1$H-NMR of 19 showed additional resonances at 1.92-2.12 ppm that correspond to the six acetyl hydrogens. As was the case for the diacyl derivative of ethyl ester disclosed above, the $^{13}$C NMR of 19 when compared to that of 14 showed downfield shifts of ~2 ppm for C-6' and C-6" (from 62.83 and 63.18 ppm in 14 to 64.89 and 65.07 ppm in 19, respectively). Further support for acetylation at both C-6' and C-6" was supported by $^{13}$C-NMR resonances at 20.90, 21.06, 172.84 (two non-resolved signals) that correspond to two acetyl CH$_3$ and two C=O groups, respectively. The assignment of protons and carbons were made by comparison of $^1$H and $^{13}$C signals of precursor 14 with 19, and by careful inspection of the $^1$H-1H COSY, $^1$H-$^{13}$C HETCOR spectra of 19. Metheine, methylene and methyl groups were distinguished by a $^{13}$C NMR DEPT spectrum of 19. Thus, Novozyme 435 was an effective catalyst for the diacetylation of 14 at C-6' and C-6" and this compound was identified as p-Hydroxy phenethyl 17-L-[(2'-O-β-D-glucopyranosyl-β-D-glucopyranosyl)-oxy-cis-9-octadecenamide-6',6"-diacetate. This study also showed that the replacement of the ethyl ester group in ethyl ester by an amide group in 14 did not have a significant effect on the Novozyme 435 catalyzed regioselective acetylation of these substrates.

The above reaction was further extended for the preparation of the corresponding dimethacrylate derivative. The Novozyme 435 mediated acryloylation of 14 using excess of vinyl methacrylate in dry THF at 50° C. for 80 hr afforded p-Hydroxy phenethyl 17-L-[(2'-O-β-D-glucopyranosyl-β-D-glucopyranosyl)-oxy-cis-9-octadecenamide-6',6"-dimethacrylate 20 ($[\alpha]^{25}_D$-3.00; m/z 900.51 [M+Na]$^+$, 878.53 [M+H]$^+$) in 88% yield. This compound had $^1$H NMR resonances similar to 19 except those that appeared due to the replacement of acetyl groups in 19 by methacryl groups in 20 at positions C-6' and C-6". Relative to 19, the $^{13}$C NMR of 20 showed downfield shifts of >2 ppm for the 6'- and 6"-carbons.

Since Novozyme 435 worked well for both amidation as well acylation, synthesis of 20 from ethyl ester by a one-pot two step process was attempted. First, the amidation of ethyl ester to form 14 was performed exactly as above. Subsequently, vinyl methacrylate was added in excess to the reaction without isolation of 14 or further change in the reaction conditions. By this method, 20 was obtained in high yield.

Novozyme 435-Catalyzed Regioselective Monoacylation of at 6'-Position.

After success in monoacylation of ethyl ester the method was extended for the synthesis of monoacyl derivative of amide 14. The sophorolipid amide 14 was treated with excess vinyl acetate in dry THF at 40° C. for 20 hr using Novozyme 435 as the catalyst. By this method, monoacetate 21 modified at the 6' position was formed in 83% yield. Also, a small amount (7%) of the corresponding diacetate 19 was found. The optically active compound 21 ($[\alpha]^{25}_D$-8.60) was identified by an LC-APCI mass spectrum (m/z 784.56 (M+H)$^+$ which is 41 mass unit higher then that for 14 indicating the presence of one acetyl groups in the molecule), and detailed NMR spectral analyses. The proton NMR of the compound showed additional resonances at 1.92-2.10 for three protons due to one acetyl groups in the molecule, which was further supported by resonances at 21.07, 172.77 in $^{13}$NMR spectrum of the molecule. Furthermore proton NMR showed, downfield shift of ~2 ppm in 6'-position (from resonance at 63.18 to 65.09 ppm) indicating acylation at this position. Monoacetylation at C-6' also resulted in an upfield shift of ~2 ppm of C-5' which is explained by the γ-effect between C-5' and the neighboring acetyl C=O atom. A downfield shift of ~2 ppm in C-2' (carbon bearing no free hydroxyl group) was also observed which might be associated with a conformational change upon acetylation at C-6'. The assignment of protons and carbons were made by comparison of $^1$H and $^{13}$C signals of precursor 14 with 21, and by careful inspection of the $^1$H-$^1$H COSY, $^1$H-$^{13}$C HETCOR spectra of 21. Metheine, methylene and methyl groups were distinguished by a $^{13}$C NMR DEPT spectrum of the molecule. The resonances in the $^1$H NMR of 21 at 5.35 ppm (m) for two protons were due to H-9 and H-10. These assignments were further supported by $^{13}$C peaks at 130.93 and 131.00 corresponding to C-9 and C-10. Thus, these results showed that Novozyme 435 was an effective catalyst for the monoacylation of 14 at C-6' and this compound was identified as p-Hydroxy phenethyl 17-L-[(2'-O-β-D-glucopyranosyl-β-D-glucopyranosyl)-oxy]-cis-9-octadecenamide-6'-acetate. Therefore, Novozym 435 is not only an excellent catalyst for highly regioselective diacylation but also monoacylation at 6'-position of 14.

The above reaction was further extended for the preparation of related monomethacrylated derivative. The Novozym 435-mediated acryloylation of 14 using excess vinyl methacrylate in dry THF at 40° C. for 20 hr afforded p-Hydroxy phenethyl 17-L-[(2'-O-β-D-glucopyranosyl-β-D-glucopyranosyl)-oxy]-cis-9-octadecenamide-6'-monomethacrylate 22 ($[\alpha]^{25}_D$-5.00; m/z 810.25 (M+H)$^+$) in 80% yield. Also a small amount of dimethacrylate 20 (7%) was formed. This compound had $^1$H NMR resonances similar to 21 except those that appeared due to replacement of an acetyl group in 21 by one methacryl group at 1.94 (3H, s), 5.63 (1H, s), 6.14 (1H, s) ppm in 22 at C-6'. The resonances in $^{13}$C NMR spectrum of 22 at 18.70, 126.71, 137.71, 137.76, 168.79 further supported the presence of a methacryl moiety in the molecule. Furthermore $^{13}$C NMR showed significant downfield shift in C-6", upfield shift of >2 ppm in C-5"-position but no change in C-2' was noticed. Metheine, methylene and methyl groups were distinguished by a $^{13}$C NMR DEPT spectrum of the molecule. Therefore, it was concluded that Novozym 435 is an excellent catalyst for regioselective monoacylation of 14 using different acylating agents.

Novozym 435-Catalyzed Regioselective Monoacylation of 14 at 6"-C.

After success in monoacylation of ethyl ester at 6"-position, the method was extended to the synthesis of similar monoacyl derivative of amide 14. For this, 14 was treated at 40° C. for 72 hr with an excess of vinyl acetate in dry THF using Lipase PS on a ceramic support (Lipase PS-C). This gave monoacetate 23, selectively modified at C-6", in 87% yield. 23 ($[\alpha]^{25}_D$-8.07) was identified by an LC-APCI mass spectrum (m/z 784.52 (M+Na)$^+$) and detailed NMR spectral analyses. The appearance in the $^1$H-NMR for 23 of additional resonance at 2.00-2.10 ppm of three protons, and the downfield shift of two protons of 14 at 3.20-3.89 (m) to 4.18 (1H, m) and 4.37 (1H, m) ppm for 23, showed the presence of one acetyl group in the molecule. $^{13}$C NMR of 23 showed a downfield shift of ~2 ppm in C-6" (64.88 ppm) compared to that for 14 (62.83 ppm). Also, there was no significant change in the peak position of C-6'. The occurrence of monoacetylation at C-6" was further supported by $^{13}$C-NMR resonances at 20.87 and 172.76 ppm corresponding to the acetyl $CH_3$ and C=O, respectively. Monoacetylation at C-6" also resulted in an upfield shift of ~2 ppm of C-5" which is due to the γ-effect. The assignment of protons and carbons were made by comparison of $^1$H and $^{13}$C signals of precursor 14 with 23, and by careful inspection of the $^1$H-$^1$H COSY, $^1$H-$^{13}$C HETCOR spectra of 23. Metheine, methylene and methyl groups were distinguished by a $^{13}$C NMR DEPT spectrum of the molecule. Also, to further substantiate the difference in the NMR spectra of 21 and 23, they were mixed in equimolar amounts. Study of the $^{13}$C DEPT 135 of this mixture showed distinctly resolved signals for 21 at 65.09 (C-6'), 62.82 (C-6") and C-2' (84.01), and for 23 at 64.88 (C-6'), 63.26 (C-6") and C-2' (81.84). No significant changes were observed for 14 and 23 in the positions of protons and carbons associated with the sophorolipid fatty acid CH=CH moiety (C-9 and C-10). Thus, these results showed that Lipase PS-C was an effective catalyst for the acetylation of 14 at C-6". 23 was identified as p-Hydroxy phenethyl 17-L-[(2'-O-β-D-glucopyranosyl-β-D-glucopyranosyl)]-oxy]-cis-9-octadecenamide-6"-acetate.

The above reaction was further extended to the preparation of related monomethacrylated derivative. The Lipase-PS-C-mediated acryloylation of 14 using excess of vinyl methacrylate in dry THF at 40° C. in 72 hr afforded p-hydroxy phenethyl 17-L-[(2'-O-β-D-glucopyranosyl-β-D-glucopyranosyl)-oxy]-cis-9-octadecenamide-6"-methacrylate 24 ([C]$^{25}_D$-4.34; m/z 832.53 (M+Na)$^+$, 810.55 (M+H)$^+$) in 88% yield. This compound had $^1$H NMR resonances similar to 23 except those that appeared due to replacement of an acetyl group in 23 by one methacryl group at 1.93 (3H, s), 5.62 (1H, s), 6.11 (1H, s) ppm in 23 at C-6". The resonances in $^{13}$C NMR spectrum of 24 at 18.57, 126.46, 137.84, 168.70 further supported the presence of a methacryl moiety in the molecule. Furthermore $^{13}$C NMR showed significant downfield shift in C-6", upfield shift in C-5" but no change in C-2' was noticed. Metheine, methylene and methyl groups were distinguished by a $^{13}$C NMR DEPT spectrum of the molecule. Also, to further substantiate the difference in the NMR spectra of 22 and 24, they were mixed in equimolar amounts. Study of the $^{13}$C DEPT 135 of this mixture showed distinctly resolved signals for 22 at 65.19 (C-6'), 62.80 (C-6") and C-2' (84.15), and for 24 at 63.28 (C-6'), 65.15 (C-6") and C-2' (81.77). Therefore, it was concluded that Lipase PS-C is an excellent catalyst for regioselective monoacylation of 14 using different acylating agents.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

TABLE 1

| | % inhibition of various fungi in presence of 5 mg/ml sophorolipid solution | | | | | | |
|---|---|---|---|---|---|---|---|
| | Hexyl SL Inhibition % | SL - Ethyl Ester Inhibition % | SL - Acid Inhibition % | SL Ethyl Ester Monoacetate Inhibition % | SL Ethyl Ester Diacetate Inhibition % | SL - Methyl Ester Inhibition % | Natural SL Inhibition % |
| Candida albicans | 38 | 20 | 24 | 100 | 100 | 100 | 30 |
| Candida antartica | 100 | 28 | 45 | 42 | 100 | 71 | 32 |
| Candida tropicalis | 100 | 35 | 40 | 35 | 100 | 100 | 25 |

What is claimed is:

1. A method for treating a fungal infection of the genus *Candida* located in or on an animal body comprising administering to a subject in need thereof a composition comprising 15 mg/ml of ethyl 17-L-[(2'-O-β-D-glucopyranosyl-β-D-glucopyranosyl)-oxy]-cis-9-octadecenoate-6',6"-diacetate sophorolipid.

2. A method for treating a fungal infection of the genus *Candida* located in or on an animal body comprising administering to a subject in need thereof a composition comprising 5 mg/ml of ethyl 17-L-[(2'-O-β-D-glucopyranosyl-β-D-glucopyranosyl)-oxy]-cis-9-octadecenoate-6',6"-diacetate sophorolipid.

3. The method for treating a fungal infection of the genus *Candida* as claimed in claim 1 or 2, wherein the ethyl 17-L-[(2'-O-β-D-glucopyranosyl-β-D-glucopyranosyl)-oxy]-cis-9-octadecenoate-6',6"-diacetate sophorolipid is produced by:

a) fermenting *Candida bombicola* in a fermentation media to form a mixture comprising lactonic 17-L-[(2'-O-β-D-glucopyranosyl-β-D-glucopyranosyl)-oxy]-cis-9-octadecenoate that has a variable degree of acetylation;

b) ring-opening the lactonic 17-L-[(2'-O-β-D-glucopyranosyl-β-D-glucopyranosyl)-oxy]-cis-9-octadecenoate with a variable degree of acetylation by reaction with ethanol under alkaline conditions;

c) diacetylating the ring-opened lactonic 17-L-[(2'-O-β-D-glucopyranosyl-β-D-glucopyranosyl)-oxy]-cis-9-octadecenoate to form open ring ethyl 17-L-[(2'-O-β-D-glucopyranosyl-β-D-glucopyranosyl)-oxy]-cis-9-octadecenoate-6',6"-diacetate sophorolipid;

d) separating the open ring ethyl 17-L-[(2'-O-β-D-glucopyranosyl-β-D-glucopyranosyl)-oxy]-cis-9-octadecenoate-6',6"-diacetate sophorolipid from the mixture to form an open ring fraction; and e) preparing the open ring ethyl 17-L-[(2'-O-β-D-glucopyranosyl-β-D-glucopyranosyl)-oxy]-cis-9-octadecenoate-6',6"-diacetate sophorolipid in the 15 mg/ml sophorolipid solution by adding 15 mg of the sophorolipid to 1 ml sucrose solution having a pH of about 8.5.

* * * * *